United States Patent
Kato et al.

(10) Patent No.: US 9,347,913 B2
(45) Date of Patent: May 24, 2016

(54) APPARATUS AND PROCESS FOR GAS SENSOR CONTROL

(71) Applicant: NGK SPARK PLUG CO., LTD., Nagoya-shi, Aichi (JP)

(72) Inventors: Akiyoshi Kato, Komaki (JP); Keiji Suzuki, Kitanagoya (JP)

(73) Assignee: NGK SPARK PLUG CO., LTD., Aichi (JP)

(*) Notice: Subject to any disclaimer, the term of this patent is extended or adjusted under 35 U.S.C. 154(b) by 273 days.

(21) Appl. No.: 14/061,973

(22) Filed: Oct. 24, 2013

(65) Prior Publication Data

US 2014/0048415 A1     Feb. 20, 2014

Related U.S. Application Data

(62) Division of application No. 12/612,979, filed on Nov. 5, 2009, now Pat. No. 8,623,186.

(30) Foreign Application Priority Data

Nov. 6, 2008   (JP) .................................. 2008-285054

(51) Int. Cl.
G01N 27/406       (2006.01)

(52) U.S. Cl.
CPC ................................... *G01N 27/4067* (2013.01)

(58) Field of Classification Search
CPC ............. G01N 27/404–27/407; G01N 27/409; G01N 27/419; G01N 27/41
USPC ........................ 204/424–429; 73/23.31–23.32
See application file for complete search history.

(56) References Cited

U.S. PATENT DOCUMENTS

| | | | |
|---|---|---|---|
| 5,974,857 A | 11/1999 | Yamashita et al. |
| 6,120,677 A | 9/2000 | Yamada et al. |
| 6,343,499 B1 | 2/2002 | Inagaki et al. |
| 6,382,015 B1 | 5/2002 | Aoki |
| 6,578,563 B2 | 6/2003 | Hada et al. |

FOREIGN PATENT DOCUMENTS

| | | |
|---|---|---|
| DE | 197 29 350 A1 | 1/1998 |
| DE | 199 21 986 A1 | 12/1999 |
| DE | 102 34 199 A1 | 3/2003 |
| JP | 10-048180 A | 2/1998 |
| JP | 2000-121600 A | 4/2000 |

OTHER PUBLICATIONS

Office Action in corresponding German Patent Application No. 10 2009 052 158.5 dated Sep. 12, 2013, together with an English translation.

*Primary Examiner* — Luan Van
*Assistant Examiner* — Maris R Kessel
(74) *Attorney, Agent, or Firm* — Sughrue Mion, PLLC

(57) ABSTRACT

A gas sensor control apparatus includes a heater regulating section to control the supply of electricity to a heater included in a gas sensor, an impedance sensing section to sense an impedance of the gas sensor cell, an impedance condition examining section to examine whether the impedance is greater than or equal to an abnormality threshold, a voltage condition examining section to examine whether a maximum effective voltage is applied to the heater, when the impedance is above the abnormality threshold, a duration measuring section to examine whether an application time duration of the maximum effective voltage becomes equal to or longer than a heater overheat preventing time, and a voltage decreasing section to decrease the heater voltage to such a lower effective voltage as to hold the temperature of the cell higher than or equal to 500° C. when the application time duration reaches the heater overheat preventing time.

3 Claims, 5 Drawing Sheets

APPARATUS AND PROCESS FOR GAS SENSOR CONTROL

CROSS-REFERENCE TO RELATED APPLICATIONS

This is a Divisional Application of U.S. application Ser. No. 12/612,979 filed Nov. 5, 2009, which claims priority from Japanese Patent Application No. 2008-285054 filed Nov. 6, 2008. The entire disclosures of the prior applications are incorporated herein by reference.

BACKGROUND OF THE INVENTION

The present invention relates to apparatus and/or process for controlling a gas sensor, such as a gas sensor including at least one cell which includes a solid electrolyte member and a pair of electrodes formed on the solid electrolyte member. Specifically, the present invention relates to a technique for sensing the impedance of a cell of the gas sensor, and controlling the supply of electricity to a heater of the gas sensor in accordance with the sensed cell impedance.

A gas sensor, such as oxygen sensor and air fuel ratio sensor, is widely used for an internal combustion engine for a motor vehicle or other applications, to improve the fuel consumption and control the combustion. Furthermore, in conjunction with the environmental concerns and tightening of regulations for limiting exhaust emissions of motor vehicles, the demand for reducing the amount of nitrogen oxides (NOx) in the exhaust gas mixture increases and drives the development of an NOx sensor capable of sensing the concentration of NOx directly. These gas sensors use a gas sensing element including one or more cells each including a solid electrolyte member of an oxygen ion conductive solid electrolyte such as zirconia, and a pair of electrodes formed on the solid electrolyte member. The gas sensing element produces an output from which the concentration of a specified gas can be determined.

As the gas sensor, there is known a full range air fuel ratio sensor (also called UEGO sensor) for sensing the oxygen concentration of a measurement gas with a construction which includes two cells (oxygen concentration sensing cell and oxygen pump cell) disposed on both sides of a measurement chamber to which a measurement gas is introduced through a diffusion resisting member. Moreover, there is known an NOx gas sensor including a cell for sensing the NOx concentration in addition to the two cells (oxygen concentration sensing cell and oxygen pump cell).

The gas sensor is connected with a sensor drive circuit for supplying electricity to a cell of the gas sensor, and arranged to sense the concentration of a specified gas in the measurement gas (gas mixture) from an output of the cell. Such a gas sensor includes a heater for heating the cell (the solid electrolyte member of the cell) to a higher temperature higher than or equal to an activation temperature so that the solid electrolyte member becomes oxygen-ion-conductive. The current supply to the heater is controlled to activate the cell quickly and to hold the cell active at temperatures equal to or higher than the activation temperature stably.

A Japanese patent document (JP 10-48180A) shows a temperature control system arranged to sense the impedance of a cell (element impedance or cell impedance) which varies in dependence on the temperature of the cell, and to control the temperature of the cell by controlling the current supply to the heater. It is possible to control the temperature of the cell by controlling the amount of electricity supplied to the heater so as to bring the impedance of the cell sensed periodically, to a desired target impedance. It is possible to sense the cell impedance by inputting a impedance sensing signal (or current) into a monitored cell whose impedance is to be sensed, and to determine the impedance from an output (response signal) of the monitored cell responsive to the impedance sensing signal.

If a wiring line leading to the monitored cell is disconnected by some trouble, the impedance of the monitored cell sensed by the control system increases excessively or infinitely. As a result, the control system misjudges that the cell (gas sensor) is cold, and continues supplying the maximum effective voltage to the heater. The continuation of application of the maximum effective voltage might increase the temperature of the gas sensor abnormally and damage the gas sensor. Therefore, a Japanese patent document (JP 2000-121600) proposes a diagnostic system for detecting an abnormal condition such as disconnection or short-circuit of gas sensing element and heater by monitoring an unusual variation of the element impedance.

SUMMARY OF THE INVENTION

However, when the abnormality is detected, the above-mentioned diagnostic system inhibits the supply of current to the heater, so that the gas sensor is cooled and foreign substance such as carbon may adhere to the surface of the sensor (the surface of the sensing element). The matter adhering to the gas sensor might obstruct the function of the gas sensing element when the normal condition is regained and the normal heater control mode is restarted. In view of such a problem, it is an object of the present invention to provide technique, such as gas sensor control apparatus and/or process, adequate for preventing improper overheating of gas sensor due to trouble such as wiring disconnection, and enabling restoration of a normal gas sensor operation. It is another object of the present invention to provide technique, such as gas sensor control apparatus and/or process, adequate for preventing improper overheating of gas sensor due to overheating of the heater when such a condition continues that an impedance of the gas sensor detected for wiring disconnection of the cell or the like, shows exceedingly high level, and preventing foreign substance such as carbon from adhering to the surface of the sensor by cooling the gas sensor without stopping the supply of current to the heater.

According to one aspect of the present invention, a gas sensor control apparatus for controlling a gas sensor for sensing a concentration of a specified gas, the gas sensor including at least one cell including a solid electrolyte member and a pair of electrodes formed on the solid electrolyte member, and serving as a monitored cell, comprises: a heater regulating section to control a supply of electricity to a heater included in the gas sensor; an impedance sensing section to sense an impedance of the (monitored) cell of the gas sensor, from an output of the cell; an impedance condition examining section to examine whether the impedance sensed by the impedance sensing section is greater than or equal to a predetermined abnormality judging threshold; a voltage condition examining section to examine whether a maximum effective voltage is applied to the heater, when the impedance is judged to be greater than or equal to the predetermined abnormality judging threshold; a duration measuring section to examine whether an application time duration of application of the maximum effective voltage to the heater becomes equal to or longer than a predetermined heater overheat preventing time; and a voltage decreasing section to command the heater regulating section to apply, to the heater, a lower effective voltage which is lower than the maximum effective voltage and which is so set as to hold the temperature of the cell higher than or equal to 500° C. when the application time duration becomes equal to or longer than the predetermined heater overheat preventing time.

According to another aspect of the invention, a gas sensor control process for controlling a gas sensor for sensing a concentration of a specified gas, the gas sensor including a heater and at least one cell including a solid electrolyte member and a pair of electrodes formed on the solid electrolyte member, and serving as a monitored cell, comprises: an impedance sensing step of sensing an impedance of the (monitored) cell of the gas sensor, from an output of the (monitored) cell; an impedance condition examining step of examining whether the impedance sensed by the impedance sensing step is greater than or equal to a predetermined abnormality judging threshold; a voltage condition examining step of examining whether a maximum effective voltage is applied to the heater, when the impedance is judged to be greater than or equal to the predetermined abnormality judging threshold; a duration measuring step of examining whether an application time duration of application of the maximum effective voltage to the heater becomes equal to or longer than a predetermined heater overheat preventing time; and a voltage decreasing step of applying a lower effective voltage which is lower than the maximum effective voltage and which is so set as to hold the temperature of the cell higher than or equal to 500° C., to the heater when the application time duration becomes equal to or longer than the predetermined heater overheat preventing time.

According to still another aspect of the present invention, a gas sensor control apparatus or process comprises part or all of the following elements (sections or steps): a heater regulating element to supply electricity or electric power to a heater included in a gas sensor for sensing a concentration of a specified gas; an impedance sensing element to sense an impedance of a (monitored) cell of the gas sensor; and a controlling element to check a first condition which is satisfied when the impedance is greater than or equal to a predetermined abnormality judging threshold, to check a second condition which is satisfied when the electric power supplied to the heater is higher than or equal to a predetermined higher power level, to measure a continuance (or time duration) of a third condition which is satisfied when the first and second conditions are both satisfied simultaneously, and to decrease the electric power or the amount of electricity supplied to the heater, from the higher power level to a lower power level lower than the higher power level when the continuance of the third condition becomes equal to or longer than a predetermined overheat preventing time. The lower power level may be so set as to hold a temperature of the gas sensor at such a higher temperature level preventing adherence of a substance contained in a gas to the gas sensor. The controlling element may comprise the following subelements (subsections or substeps): a first subelement to check the first condition, a second subelement to check the second condition, a third subelement to measure the continuance of the third condition, and a fourth subelement to decrease the electric power to the lower power level when the continuance of the third condition becomes equal to or longer than the predetermined overheat preventing time.

DETAILED DESCRIPTION OF THE INVENTION

Figure 1:
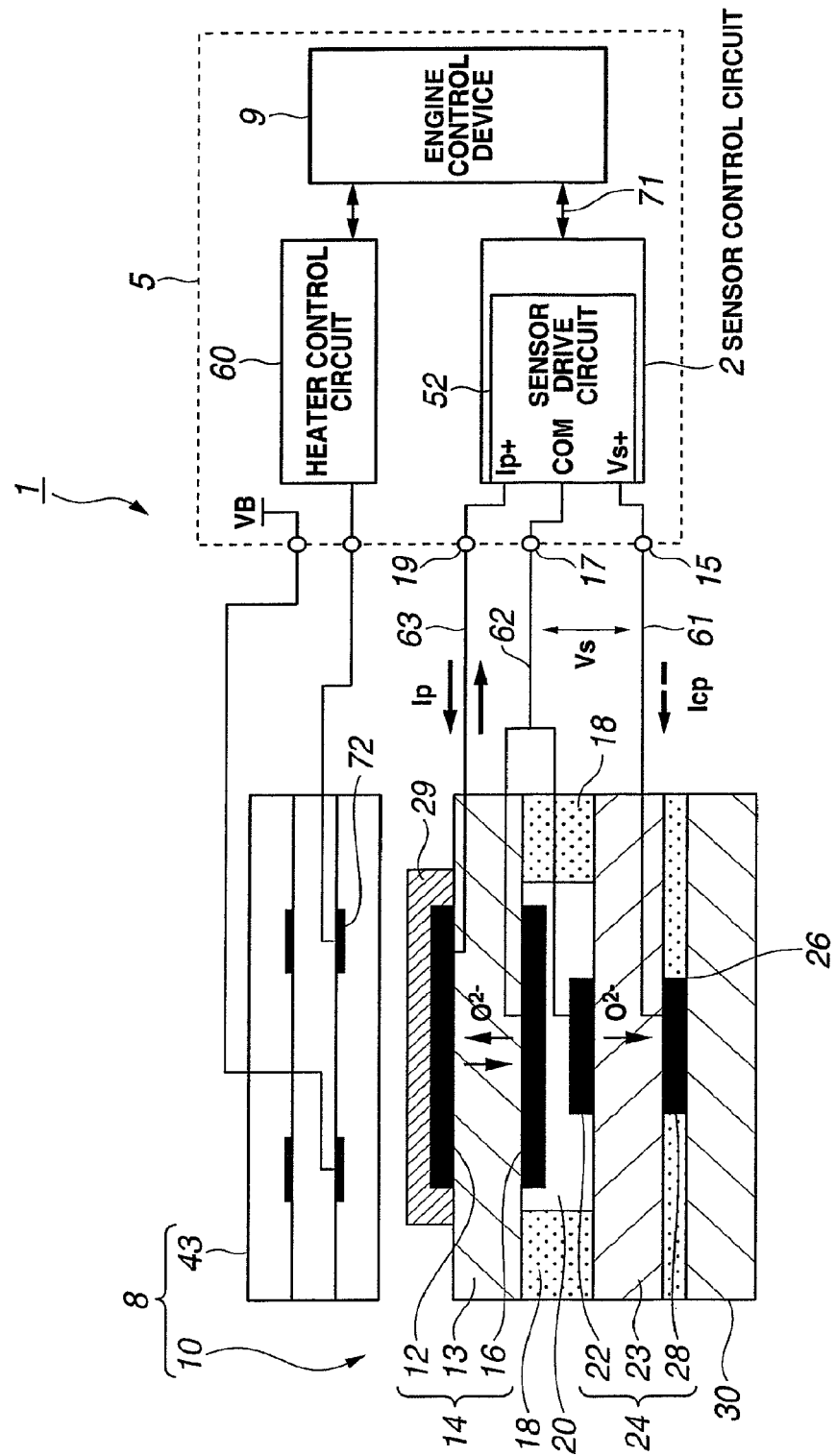
FIG. 1 is a schematic view showing a gas sensor control system according to an embodiment of the present invention, forming at least a part of an internal combustion engine control system.

FIG. 1 schematically shows a control system 1 including a gas sensor control unit (electronic control unit ECU) 5. The control system 1 of this example is constructed as an internal combustion engine control system performing various control operations to control one or more operating conditions of an internal combustion engine (engine), and operations for sensing a specified gas component (such as oxygen) in a measurement gas (such as exhaust gas mixture) to be examined.

This control system 1 includes the electronic control unit 5 and a gas sensor 8 attached to an exhaust pipe of the engine. Electronic control unit 5 includes a sensor control circuit 2 for controlling the gas sensor 8 (sensing element 10), an engine control device 9 (hereinafter referred to as engine CPU 9), and a heater control circuit 60 for controlling a heater (or heating element) 43. The sensor control circuit 2 includes a sensor drive circuit 52. The engine control device 9 is connected with the heater control circuit 60, and configured to control the heater control circuit 60 so as to control the temperature of sensing element 10 to an operation temperature (or activation temperature). The engine control device 9 is connected with the sensor control circuit 2 through a transmission cable 71, and configured to control the sensor control circuit 2.

The gas sensor 8 includes the sensing element 10 for sensing the oxygen concentration in a wide range in the measurement gas (exhaust gas mixture) which is the gas under measurement, and the heater or heating element 43 for holding the temperature of sensing element 10 at the operation temperature. This gas sensor 8 functions as a full range air fuel ratio sensor. The sensing element 10 includes an oxygen pump cell 14, a porous diffusion layer 18, an sensing cell 24, and a reinforce plate 30, as mentioned more in detail later.

The sensor control circuit 2 includes the sensor drive circuit 52 connected electrically with gas sensor 8, and other circuits. The sensor drive circuit 52 controls gas sensor 8 by supplying electricity to gas sensor 8 (oxygen pump cell 14 and sensing cell 24), and senses an output signal of oxygen pump cell 14 (gas sensor signal) and an element impedance (an impedance signal Vrpvs varying with the element impedance of the oxygen concentration sensing cell 24, in this example). Sensor control circuit 2 delivers the gas sensor signal and the element impedance signal to the engine control device 9. In this example, oxygen concentration sensing cell 24 is a cell whose impedance is to be sensed, and hence oxygen concentration sensing cell 24 can serve as "(impedance) monitored cell".

The sensor control circuit 2 can be realized in the form of ASIC (application specific integrated circuit), for example. The gas sensor signal is a signal which varies in dependence on the oxygen concentration of the measurement gas, and which is used for sensing the oxygen concentration. The element impedance (impedance signal) represents the electric resistance of gas sensor 8 which varies with the temperature of gas sensor 8. The gas sensor 8 (heater 43) is controlled in accordance with the element impedance, as mentioned later more in detail.

The sensor control circuit 2 (sensor drive circuit 52) includes a Vs+ terminal, a COM terminal and an Ip+ terminal which are connected, respectively, with a first connection terminal 15, a second connection terminal 17 and a third connection terminal 19 electrically. The Vs+ terminal of sensor control circuit 2 is connected, through first connection terminal 15 and a wiring line 61, to a later-mentioned second sensing electrode 28 of sensing element 10. The COM terminal of sensor control circuit 2 is connected, through second connection terminal 17 and a wiring line 62, to a first sensing electrode 22 and a second pump electrode 16 of sensing element 10. The Ip+ terminal of sensor control circuit 2 is connected, through third connection terminal 19 and a wiring line 63, to a first pump electrode 12 of sensing element 10. Thus, sensor drive circuit 52 is connected with gas sensor 8, and configured to receive the gas sensor signal and the impedance signal.

In the following explanation, no distinction is made between the Vs+ terminal and first connection terminal 15, between the COM terminal and second connection terminal 17 and between the Ip+ terminal and third connection terminal 19. In the following explanation, "Vs+ line" is used, according to the need, to denote the portion causing an excessive increase of the element impedance if a wiring trouble or abnormality (such as disconnection or breakage of wiring line) occurs in the portion. The Vs+ line includes at least the wiring lines 61 and 62 extending from the sensing electrodes 28 and 22 of oxygen concentration sensing cell 24 for sensing the element impedance, and the wiring section of the sensor drive circuit 52 connected with the wiring lines 61 and 62. A control section 55 can be constructed as an analog switching circuit, for example.

The engine control device 9 can be composed of a microcomputer including a central processing unit CPU, a memory section (RAM and ROM) for storing information such as data and programs, and input and output ports for inputting and outputting signals from and to external device or devices. In engine control device 9, CPU performs various computer operations according to a program stored in the memory section and controls the calculation, data transfer and the execution of instructions. Furthermore, engine control device 9 reflects a signal inputted to the input port on the contents of an input port register, and supplies the contents stored in an output port register, as a signal, to the output port.

In accordance with the gas sensor signal Vip outputted from sensor control circuit 2, the engine control device 9 determines or judges the energizing condition or the current supply condition (such as the current direction and the current magnitude) of an Ip current flowing through oxygen pump cell 14, and calculates the oxygen concentration from the energizing condition of the Ip current. By using the calculated oxygen concentration, the engine control device 9 controls the combustion and other operating conditions of the engine.

In accordance with the impedance signal Vrpvs outputted from sensor control circuit 2, the engine control device 9 calculates the impedance Rpvs of oxygen concentration sensing cell 24, and performs a heater current control process of outputting a heater current command for heater 43 in accordance with the calculated impedance Rpvs, to heater control circuit 60. In one of possible interpretations, this heater current command corresponds to "command", and the engine control device 9 corresponds to "impedance abnormality judging means", "voltage application judging means", "voltage applying state judging means", "commanding means", "activation judging means", and "time setting means", and can serve as at least part of "impedance condition examining section", "voltage condition examining section", "duration measuring section", "voltage decreasing section", "activation judging section", and "time setting section". The heater control circuit 60 and engine control circuit 9 correspond to "heater controlling means", and can serve as at least part of "heater regulating section". The sensor control circuit 2 and engine control device 9 correspond to "impedance sensing means" and can serve as at least part of "impedance sensing section".

The gas sensor 8 has the following construction as shown in FIG. 1. The oxygen pump cell 14 includes a solid electrolyte member 13 shaped like a plate, and first and second pump electrodes 12 and 16 formed, respectively, on front and rear surfaces of solid electrolyte member 13. The solid electrolyte member 13 is made of an oxygen ion conductive solid electrolyte. In this example, solid electrolyte member 13 is made of a partially stabilized zirconia (ZrO2). First and second pump electrodes 12 and 16 are made of material containing platinum, as main component. First pump electrode 12 is electrically connected, through wiring line 63, with the third connection terminal 19 of electronic control unit 5. Second pump electrode 16 is electrically connected, through wiring line 62, with the second connection terminal 17 of electronic control unit 5. First pump electrode 12 is covered with a porous protective layer 29 protecting first pump electrode 12 against poisonous substance.

The oxygen concentration sensing cell 24 includes a plate-shaped solid electrolyte member 23, and first and second sensing electrodes 22 and 28 formed, respectively, on front and rear surfaces of solid electrolyte member 23. The solid electrolyte member 23 is made of an oxygen ion conductive solid electrolyte. In this example, solid electrolyte member 23 is made of partially stabilized zirconia (ZrO2). First and second sensing electrodes 22 and 28 are made of material containing platinum, as main component. First sensing electrode 22 is electrically connected, through wiring line 62, with the second connection terminal 17 of electronic control unit 5, and further connected with second pump electrode 16. Second sensing electrode 28 is electrically connected, through wiring line 61, with the first connection terminal 15 of electronic control unit 5.

A porous diffusion layer 18 is provided in a part of an insulating layer (not shown) which is formed between oxygen pump cell 14 and oxygen concentration sensing cell 24, and which is made mainly of an insulating material (such as alumina) for electrically insulating both cells 14 and 24 from each other. Porous diffusion layer 18 is a porous layer made mainly of an insulating material (such as alumina) for controlling diffusion of measurement gas introduced into sensing element 10. Instead of porous diffusion layer 18, it is optional to form small hole or holes in a side wall of the above-mentioned insulating layer, as a diffusion control section.

A measurement chamber 20 is a hollow portion surrounded by the porous diffusion layer 18 and the above-mentioned insulating layer, between oxygen pump cell 14 and oxygen concentration sensing cell 24. This measurement chamber 20 is in communication with a measurement gas atmosphere through porous diffusion layer 18 (or porous section). The second pump electrode 16 is bared in an upper portion of measurement chamber 20, and the first sensing electrode 22 is bared in a lower portion of measurement chamber 20.

The reinforce plate 30 is attached to the rear side surface of oxygen concentration sensing cell 24, opposite to the front side surface facing to the measurement chamber 20, so as to form a laminate to increase the strength of sensor element 10 as a whole. Reinforce plate 30 is made of a material containing, as a main component, ceramic, and shaped in the form of plate approximately equal in size to the solid electrolyte members 13 and 23.

The second sensing electrode 28 is sandwiched between the reinforce plate 30 and oxygen ion conductive solid electrolyte member 23, and shielded from the outside. A reference oxygen chamber 26 is formed in the form of a sealed space, around the second sensing electrode 28. Therefore, it is possible to accumulate oxygen at a substantially constant concentration in the reference oxygen chamber 26 by supplying a minute constant current Icp in a direction from second sensing electrode 28 toward first sensing electrode 22 and pumping oxygen from measurement chamber 20 toward second sensing electrode 28. Thus, the oxygen concentration in reference oxygen chamber 26 is used as a reference oxygen concentration in sensing the actual oxygen concentration.

The heater 43 in the form of a flat plate is disposed so as to confront the oxygen pump cell 14 of sensing element 10. Heater 43 is made of a material containing alumina as a main component, and includes therein a heater wire 72 made of a material containing platinum as a main component. Heater 43 is controlled by electric power supplied from heater control circuit 60 so as to control the temperature of sensing element 10 to the target activation temperature (830° C., in this example). One end of the heater wire 72 is electrically connected with heater control circuit 60. The other end of heater wire 72 is connected with a battery VB (12V battery in this example). By heating, the heater 43 activates the sensing element 10 (oxygen pump cell 14 and oxygen concentration sensing cell 24), and enables a gas sensing (oxygen sensing) action.

The thus-constructed gas sensor 8 (sensing element 10) is operated in the following manner. First, the measurement gas (exhaust gas in this example) diffuses through porous diffusion layer 18 into measurement chamber 20. If then air fuel mixture supplied to the engine (or the measurement gas in measurement chamber 20) is held at the theoretical air fuel ratio, an electromotive force of 450 [mV] is produced in oxygen concentration sensing cell 24 by an oxygen concentration difference between the measurement chamber 20 and reference oxygen chamber 26 providing the reference oxygen concentration. (A potential difference of 450 [mV] is produced between the first and second sensing electrodes 22 and 28.)

In dependence on variation in the air fuel ratio of the air fuel mixture supplied to the engine, the concentration of oxygen contained in the exhaust gas varies, and hence the oxygen concentration of the measurement gas in measurement chamber 20 is varied. Therefore, the engine control system 1 of this example controls the Ip current flowing through the oxygen pump cell 14 with the sensor control circuit 2 so as to hold the potential difference between the first and second sensing electrodes 22 and 28 at 450 [mV]. Thus, by controlling the Ip current so as to control the atmosphere in measurement chamber 20 at the same condition as the theoretical air fuel ratio, the control system causes the oxygen pump cell 14 to perform an oxygen pumping action.

The oxygen pump cell 14 is arranged to be switched between an operation of drawing oxygen from measurement chamber 20 and an operation of delivering oxygen into measurement chamber 20 in response to the direction of current supplied between the electrodes (first and second pump electrodes 12 and 16). Moreover, the oxygen pump cell 14 is capable of adjusting the pumping quantity of oxygen in accordance with the magnitude of the current supplied between the electrodes. Therefore, engine control device 9 can calculate the oxygen concentration of the measurement gas in accordance with the current condition (such as the current direction and the current magnitude) of the Ip current.

Figure 2:
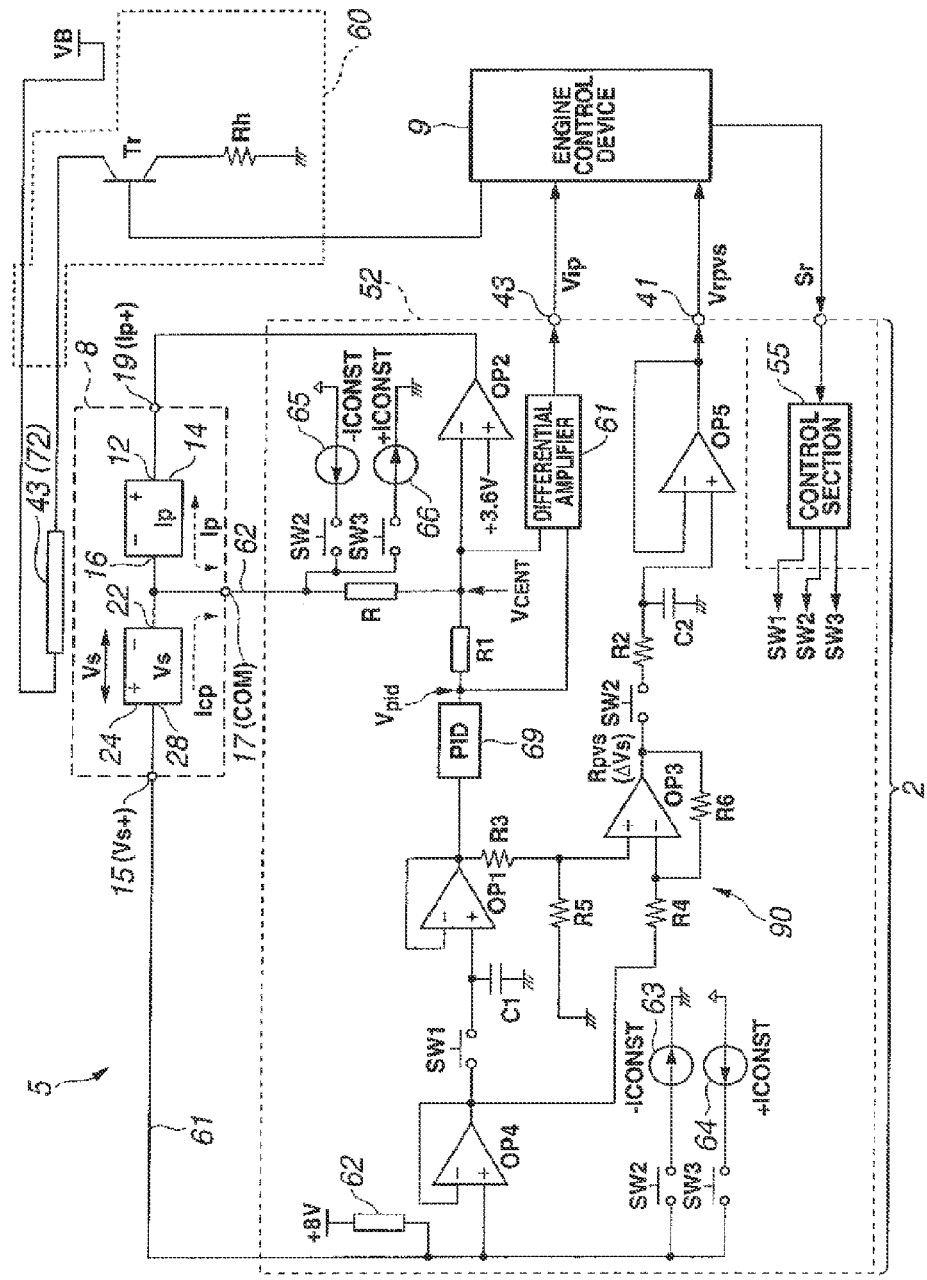
FIG. 2 is a circuit diagram schematically showing the construction of an electronic control unit in the gas sensor control system of FIG. 1.

FIG. 2 is a circuit diagram schematically showing the electronic control unit 5, for explaining the construction and operations of electronic control unit 5. As mentioned before, the electronic control unit 5 includes the sensor control circuit 2, heater control circuit 60 and engine control device 9. The sensor control circuit 2 includes the sensor drive circuit 52 and control section 55.

The heater control circuit 60 includes a transistor Tr including a collector connected with one end of the heating resistive element 72, an emitter grounded through a resistor Rh, and a base connected with the engine control device 9. Therefore, by outputting a signal of a voltage level turning on the transistor Tr (a heater on signal or "command") to the base of transistor Tr, the engine control device can cause a current to flow through the heating resistive element 72 by supplying a voltage from the battery VB, and thereby generate heat with the heater 43. When the engine control device 9 stops outputting the heater on signal, the transistor Tr turns off, and stops supplying current to the heating resistive element 72, so that the heating operation of heater 43 is terminated.

In this example, the voltage applied to heater 43 is controlled by setting the duty ratio (or duty cycle) to 100% when the maximum effective voltage (=the source voltage of battery VB which is 12V in this example) is to be applied to heater 43, and by varying the duty ratio between 0%~100% when a voltage lower than the maximum effective voltage is applied. For this control, the engine control device 9 delivers the above-mentioned heater on signal determined by the duty ratio, to heater control circuit 60, and the heater control circuit 60 is operated in an on-off mode in response to the heater on signal. Thus, this system controls the current supply to heater 43 by PWM.

The sensor drive circuit 52 has the following circuit configuration mainly for measuring the oxygen concentration. Sensor drive circuit 52 includes an operational amplifier OP2, a PID control circuit 69 and a constant current circuit 62. Operational amplifier OP2 is for flowing the Ip current to drive the oxygen pump cell 14. PID control circuit 69 is a circuit for improving the control characteristic of Ip current. Constant current circuit 62 is a circuit for supplying the constant current Icp to oxygen concentration sensing cell 24 to hold constant the oxygen concentration around the second sensing electrode 28 (in the reference oxygen chamber 26).

Sensor drive circuit 52 further includes switches SW1~SW3 for changing the operation state of sensor drive circuit 52 in accordance with switch command signals outputted from engine control device 9. In accordance with changes in the on/off states of switches SW1~SW3, the sensor drive circuit 52 can perform an operation to supply the sensor signal to sense the impedance signal Vrpvs, an operation to sense the impedance signal Vrpvs, and various other operations to control the current supply to heater 43 and to sense the temperature of gas sensor 8.

Moreover, sensor drive circuit 52 includes a Vcent point connected with the COM terminal 17. The output terminal of PID control circuit 69, the inverting input terminal of operational amplifier OP2, and one of input terminals of differential amplifier circuit 61 are connected to the Vcent point. The output terminal of PID control circuit 69 is connected through a sensing resistor R1, to the Vcent point. A reference voltage of 3.6V is applied to the non-inverting input terminal of operational amplifier OP2. The output terminal of operational amplifier OP2 is connected to the Ip+ terminal. Thus, operational amplifier OP2 forms a part of a negative feedback circuit for controlling the current supply to sensing element 10 (oxygen pump cell 14, to be exact).

The other input terminal of differential amplifier circuit 61 is connected with a junction point (Vpid point) between the output terminal of PID control circuit 69 and the sensing resistor R1. The differential amplifier circuit 61 is configured to amplify a voltage difference between both ends of sensing resistor R1. The second pump electrode 16 is connected to the Vcent point through resistor R, wiring line 62 and second connection terminal (COM terminal) 17.

The PID control circuit 69 performs a PID calculation of a deviation $\Delta Vs$ between the control target voltage of 450 mV for oxygen concentration sensing cell 24, and the output voltage Vs of oxygen concentration sensing cell 24 and thereby performs the function of the negative feedback control to improve the control characteristic. The input terminal of PID control circuit 69 is connected through an operational amplifier OP1, with the output terminal of an operational amplifier OP4 whose non-inverting input terminal is connected with the Vs+ terminal 15. Thus, the output voltage Vs of oxygen concentration sensing cell 24 is inputted, through operational amplifier OP4, into PID control circuit 69. The inverting input terminal of operational amplifier OP4 is connected with its own output terminal.

The constant current circuit 62 connected with the Vs+ terminal 15 includes a resistor connected in series with a constant voltage source (denoted by 8V in FIG. 2). Constant current circuit 62 is arranged to supply the constant current Icp (of 17 µA, for example) to oxygen concentration sensing cell 24 to hold the oxygen concentration constant around second sensing electrode 28 of oxygen concentration sensing cell 24 (in reference oxygen chamber 26).

These circuits are arranged to sense the oxygen concentration in the following manner. First, the sensor drive circuit 52 supplies the minute constant current Icp to oxygen concentration sensing cell 24 with constant current circuit 62, and simultaneously controls the pump current Ip flowing through oxygen pump cell 14 so as to control the voltage Vs between both ends of oxygen concentration sensing cell 24 (between the Vs+ terminal and the COM terminal) to 450 mV. By so doing, the sensor drive circuit 52 draws oxygen into and out of the measurement chamber 20. That is, sensor drive circuit 52 adjusts the oxygen concentration (oxygen partial pressure) in measurement chamber 20 with the oxygen pump cell 14 so as to bring the voltage Vs across the oxygen concentration sensing cell 24 to 450 mV.

The magnitude and direction of pump current Ip flowing through oxygen pump cell 14 are varied in dependence on the oxygen concentration (air fuel ratio) of the exhaust gas. Therefore, it is possible to calculate the oxygen concentration in the exhaust gas by sensing this pump current Ip with sensing resistor R1 and by using the gas sensor signal Vip obtained by the differential amplification of the voltage across this sensing resistor R1. The reference oxygen chamber 26 can be used as an internal oxygen reference source by the flow of minute current Icp through oxygen concentration sensing cell 24 in the direction to draw oxygen from measurement chamber 20 toward porous electrode 28.

PID control circuit 69 is configured to control the pump current Ip in the PID control mode to control the potential difference to 450 mV between the potential at the Vs+ terminal of oxygen concentration sensing cell 24 connected through first operational amplifier OP1 and the potential at the COM terminal (Vcent point). In this example, the result of the PID calculation of PID control circuit 69 based on the deviation between the target control voltage (450 mV) and the voltage Vs across oxygen concentration sensing cell 24 is fed back to second operational amplifier OP2, and the second operational amplifier OP2 supplies the pump current Ip to oxygen pump cell 14.

The sensing resistor R1 is arranged to sense the magnitude of pump current Ip and to convert into a voltage signal. The voltage between both ends of this sensing resistor R1 (the difference between the potential at the Vcent point and the potential at the Vpid point) is differential-amplified with a predetermined amplification degree by the differential amplifier 61, and supplied as the gas sensor signal Vip, from a signal output terminal 43 to engine control device 9.

Engine control device 9 converts the gas sensor signal Vip to a digital signal with an A/D converter circuit (not shown). Thereafter, engine control device 9 performs the concentration calculating process to calculate the oxygen concentration corresponding to the gas sensor signal Vip by using a functional relationship in the form of map (or maps) or mathematical expression (or expressions).

Sensor drive circuit 52 has the following circuit configuration mainly used for sensing the impedance Rvps of oxygen concentration sensing cell 24.

The non-inverting input terminal of first operational amplifier OP1 is connected, through a first capacitor C1 and the first switch SW1, with the output terminal of fourth operational amplifier OP4. First operational amplifier OP1, first capacitor C1 and first switch SW1 form a sample and hold circuit. This sample hold circuit turns the first switch SW1 from ON to OFF at the time of impedance sensing of oxygen concentration sensing cell 24 and thereby hold the voltage Vs (the potential at the Vs+ terminal) produced across the oxygen concentration sensing cell 24 just before the current supply for sensing the impedance of oxygen concentration sensing cell 24. By so doing, the sample hold circuit inputs the voltage Vs just before the detection of the impedance, to the PID control circuit 69.

One end of first capacitor C1 is connected with the junction point between first switch SW1 and the non-inverting input terminal of first operational amplifier OP1. The other end of first capacitor C1 is grounded.

The output terminal of first operational amplifier OP1 is connected, through a resistor R3, with the non-inverting input terminal (+ terminal) of third operational amplifier OP3. Moreover, one end of resistor R5 is connected with the junction point between the resistor R3 and the non-inverting input terminal of third operational amplifier OP3. The other end of resistor R5 is grounded.

The inverting input terminal of third operational amplifier OP3 is connected, through a resistor R4, with the output terminal of fourth operational amplifier OP4, and further connected with the output terminal of third operational amplifier OP3 itself through a resistor R6. Therefore, the inverting input terminal of third operational amplifier OP3 receives the Vs+ potential (the potential at the Vs+ terminal) at the time of supply of a later-mentioned current −Iconst for sensing the impedance, to oxygen concentration sensing cell 24.

Third operational amplifier OP3 outputs a voltage variation $\Delta Vs$ corresponding to a difference between the hold value held by first operational amplifier OP1 (the voltage Vs of oxygen concentration sensing cell 24 immediately before the supply of current for sensing the impedance) and the Vs+ potential at the time of supply of the impedance sensing current −Iconst to oxygen concentration sensing cell 24 (the output potential of fourth operational amplifier OP4). Since this voltage variation $\Delta Vs$ is approximately proportional to a bulk resistance of oxygen concentration sensing cell 24, this voltage variation $\Delta Vs$ can be used as the impedance signal Vrpvs representing the impedance of oxygen concentration sensing cell 24. Thus, third operational amplifier OP3 outputs the voltage variation ΔVs and outputs the impedance signal Vrpvs approximately proportional to the bulk resistance of oxygen concentration sensing cell 24.

In this sensor control device 5, the third operational amplifier OP3 and resistors R3~R6 form a differential amplifying type operational amplifier circuit (that is, differential amplifier circuit) 90. Thus, the operational amplifier circuit 90 for sensing the impedance is of the differential amplifying type which can remove noises inputted to the two input terminals in common, and therefore, the sensor control device 5 can produce the adequate impedance signal Vrpvs receiving little influence from noises.

The output terminal of operational amplifier 90 (third operational amplifier OP3) is connected, through second switch SW2 and resistor R2, with the non-inverting input terminal of fifth operational amplifier OP5. The inverting input terminal of fifth operational amplifier OP5 is connected with the output terminal of fifth operational amplifier OP5 itself, to receive the output of fifth operational amplifier OP5. One end of second capacitor C2 is connected with the junction point between resistor R2 and the non-inverting input terminal of fifth operational amplifier OP5. The other end of second capacitor C2 is grounded. The output terminal of fifth operational amplifier OP5 is connected, through the signal output terminal 41, with the engine control device 9.

The fifth operational amplifier OP5, second capacitor C2, second switch SW2 and resistor R2 form a signal hold circuit. The voltage variation ΔVs is inputted from third operational amplifier OP3 to this signal hold circuit when second switch SW2 is turned from OFF to ON at the time of sensing the impedance of oxygen concentration sensing cell 24. Thereafter, when second switch SW2 is turned from ON to OFF, the signal hold circuit retains the voltage variation ΔVs outputted from third operational amplifier OP3 at the time of the on state of second switch SW2, with second capacitor C2, and delivers impedance signal Vrpvs representing the voltage variation ΔVs to engine control device 9.

Then, engine control device 9 converts the impedance signal Vrpvs to the digital signal with the A/D converter (not shown), and thereafter performs the temperature sensing process of calculating the impedance of oxygen concentration sensing cell 24, and hence the temperature of gas sensor 8, by using the map or mathematical expression retained in engine control device 9.

A current source 63 is connected, through a second switch SW2, with the Vs+ terminal 15. A current source 65 is connected, through another second switch SW2, with the junction point between the resistor R and COM terminal 17. These current sources 63 and 65 are a source for supplying the constant current −Iconst to sense the impedance of oxygen concentration sensing cell 24.

Similarly, a current source 64 is connected, through third switch SW3, with the Vs+ terminal 15. A current source 66 is connected, through another third switch SW3, with the junction point between the resistor R and COM terminal 17. These current sources 64 and 66 are a source for supplying the constant current +Iconst which is opposite in polarity to the impedance sensing constant current −Iconst.

The (switch) control section 55 is a circuit for controlling the switching states (on/off states) of these first, second and third switches SW1~SW3. After receipt of a notification signal Sr signaling a start of the temperature sensing process from engine control device 9, the control section 55 is operated to control the states of the switches SW1~SW3 according to a timer count of a timer circuit provided in control section 55.

The first switch SW1 is arranged to control a voltage holding operation of first operational amplifier OP1 (sample hold circuit). Second switches SW2 are arranged to control the on/off state of the constant current −Iconst for sensing the impedance of oxygen concentration sensing cell 24, and to control the signal hold operation of fifth operational amplifier OP5 (the signal hold circuit). The third switches SW3 are arranged to control the on/off state of the constant current +Iconst opposite to the constant current −Iconst in polarity.

Figure 3:
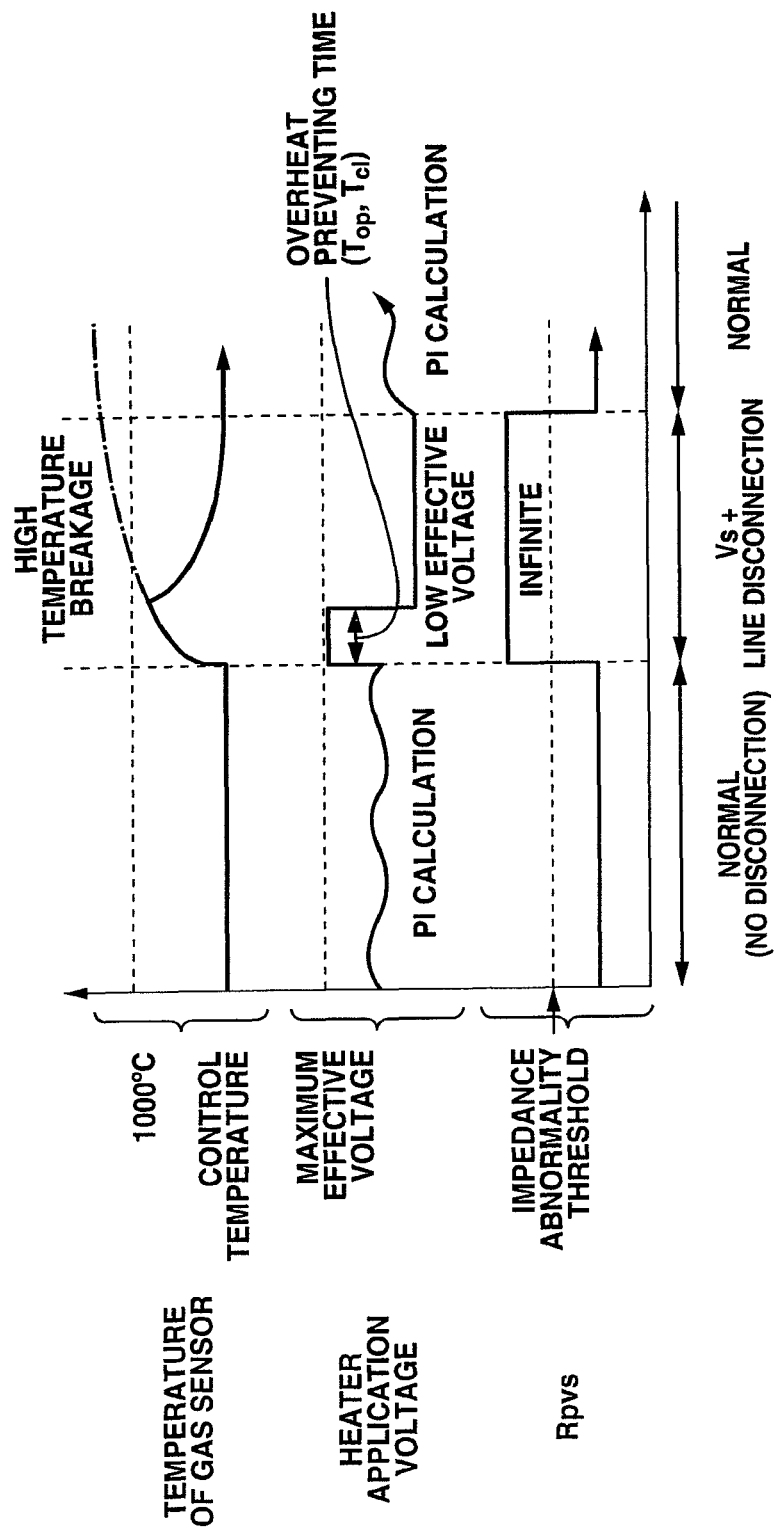
FIG. 3 is a graphic view for illustrating an overheat preventing process performed by the gas sensor control system of FIG. 1.

FIG. 3 shows a main characteristic portion of this embodiment according to the present invention, in the form of a graph illustrating the overheat preventing process performed by engine control device 9. In this embodiment, if the impedance Rpvs of oxygen concentration sensing cell 24 becomes greater than or equal to an abnormality judging threshold (threshold value of the impedance for judging abnormality) because of a trouble such as a disconnection of the Vs+ line of oxygen concentration sensing cell 24, the control system (i) terminates the application of the maximum effective voltage to heater 43 at the timing when the application time becomes equal to a predetermined overheat preventing time (or time period), and (ii) supplies a current to the heater 43 with a low (or lower) effective voltage which is lower than the maximum effective voltage and which is adequate for making the temperature of oxygen concentration sensing cell 24 higher than or equal to 500° C. (or making the impedance Rvps of oxygen concentration sensing cell 24 equal to a value corresponding a temperature higher than or equal to 500° C.).

When the Vs+ line of oxygen concentration sensing cell 24 is broken, and hence the impedance becomes excessively or infinitely great, the control system misjudges that the temperature of oxygen concentration sensing cell 24 is too low, and continues the application of the maximum effective voltage to heater 43, as shown in FIG. 3. As a result, the temperature of gas sensor 8 might be increased abnormally (beyond 1000° C., as shown by a one dot chain line in FIG. 3), resulting in breakage.

If the Vs+ line is short-circuited with the ground potential, the control system is unable to detect the signal itself. Therefore, the control system can detect the occurrence of an abnormal condition immediately, and responds to the abnormal condition adequately according to another process.

Therefore, when the impedance Rpvs of oxygen concentration sensing cell 24 becomes greater than or equal to the abnormality judging threshold (400Ω, in this example), the control system of this embodiment prevents overheat of gas sensor 8 (as shown by a solid line in FIG. 3) by limiting the application time (duration) of the maximum effective voltage to heater 43 to the predetermined heater overheat preventing time (Top, Tc1).

After the expiration of the heater overheat preventing time, the control system applies the lower effective voltage lower than the maximum effective voltage to heater 43. Thus, instead of cutting off the current supply to heater 43 in response to the occurrence of the abnormal condition, the control system continues the heating operation with the lower voltage to hold a temperature for preventing the gas sensor 8 (sensing element 10) from becoming cool and thereby preventing foreign matter (such as carbon) from adhering to the surface of sensing element 10.

When the impedance Rpvs of oxygen concentration sensing cell 24 becomes lower than the abnormality judging threshold, the control system resumes the normal heater control operation based on the PI calculation. By this PI calculation which is known per se, the control system calculates the heater application voltage to hold the temperature of gas sensor 8 constant, from the difference ΔRpvs between the target value of impedance Rpvs and the value of impedance Rpvs at the time of operation of a later-mentioned step S18.

In this example, the lower effective voltage is set at a voltage (8V in this example) for controlling the temperature of oxygen concentration sensing cell 24 equal to or higher than the predetermined temperature (500° C. in this example) which is effective for preventing adherence of undesired substance such as carbon in the exhaust gas onto the surface of sensing element 10. If the lower effective voltage is set at such a level as to hold the temperature of oxygen concentration sensing cell 24 higher than or equal to 700° C., then it is possible to prevent adherence of substances such as phosphorous, silicon and lead. A preferable range of the temperature of oxygen concentration sensing cell 24 is 750° C.~900° C., and preferably, the lower effective voltage is set at such a level to hold the temperature of oxygen concentration sensing cell 24 within this temperature range. It is possible to measure the temperature of oxygen concentration sensing cell 24 from the impedance Rpvs of oxygen concentration sensing cell 24.

The heater overheat preventing time can be determined experimentally on the basis of the results of experiment for measuring an amount of time until the temperature is increased to 1000° C. by the continuation of application of the maximum effective voltage. The length of the allowable heater overheat preventing time is varied in dependence on the condition (such as the temperature) of gas sensor 8 before the application of the maximum effective voltage. Accordingly, this example employs a time (amount of time) Top from a start of application of the maximum effective voltage in the state in which the gas sensor 8 is at normal temperature, until the temperature of gas sensor 8 becomes equal to 1000° C. (second continuation value or second amount of time), and a time (amount of time) Tc1 from a start of application of the maximum effective voltage in the state in which gas sensor 8 is at a target operating temperature (temperature at the PI control, 830° C.), until the temperature of gas sensor 8 becomes equal to 1000° C. (first continuation value or first amount of time). Bt setting the heater overheat preventing time in this way, the control system can prevent overheating of gas sensor 8 more accurately. The second continuation value (Top) is longer than the first continuation value (Tc1). In this example, the impedance Rpvs is about 75Ω when gas sensor 8 is at the target operating temperature (830° C., in this example).

Figure 4:
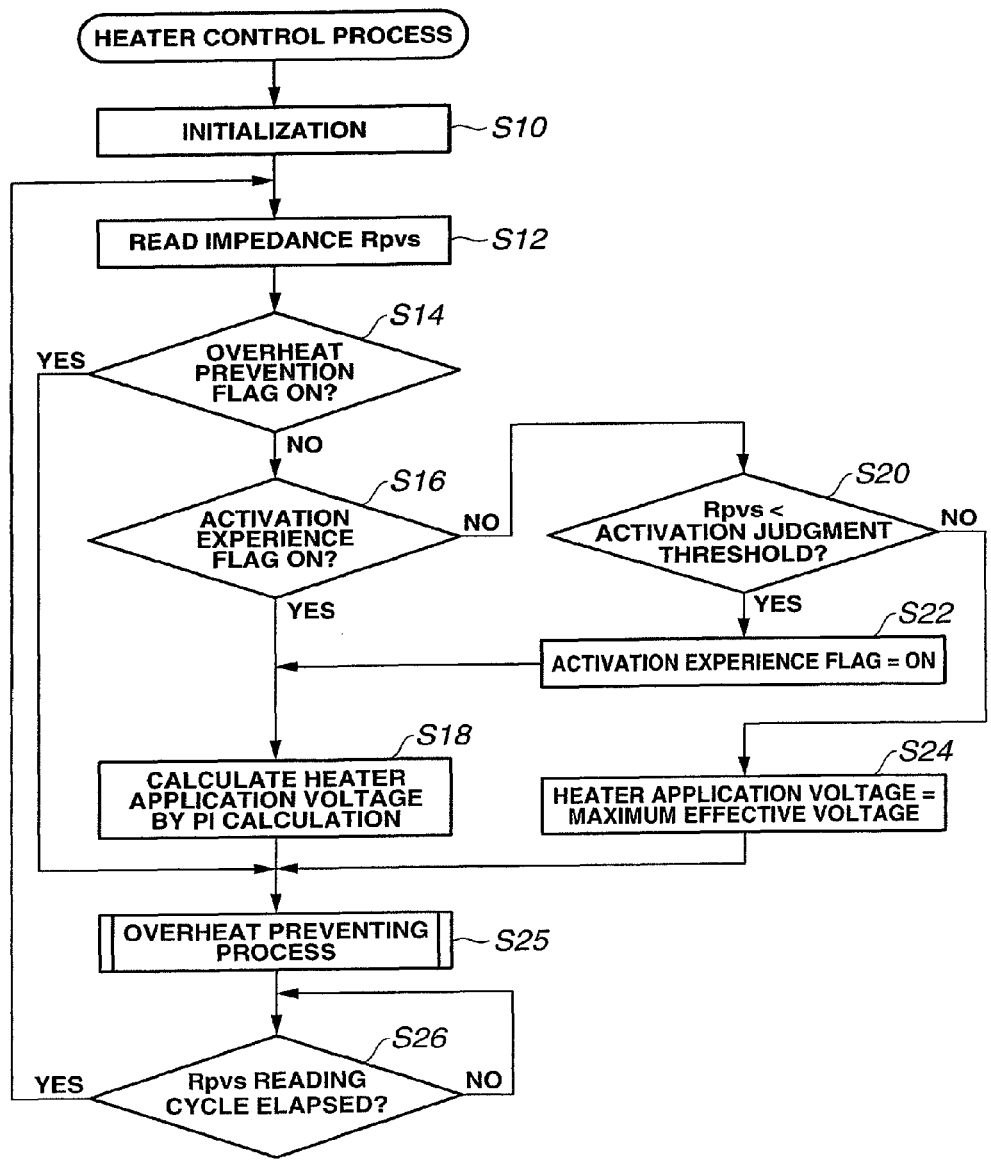
FIG. 4 is a flowchart showing a heater control process performed by the gas sensor control system of FIG. 1.
Figure 5:
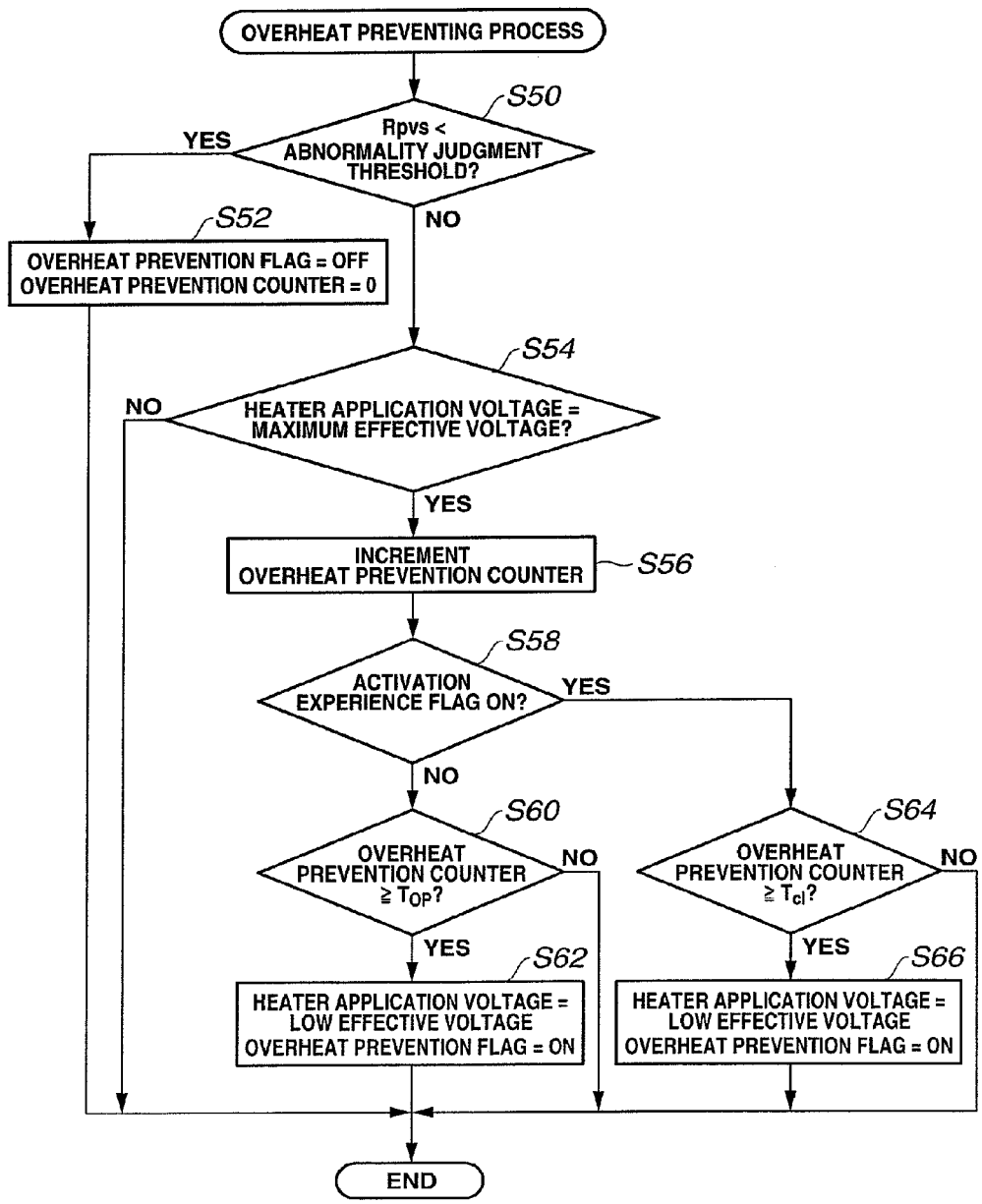
FIG. 5 is a flowchart showing the overheat preventing process performed by the gas sensor control system of FIG. 1.

FIGS. 4 and 5 show the heater control process and the heater overheat preventing process performed by engine control device 9. In this example, the heater control process shown in FIG. 4 is performed as a main routine, and the heater overheat preventing process shown in FIG. 5 is performed as a subroutine. Simultaneously with the heater control process, the engine control device 9 performs the temperature sensing process for sensing the temperature of gas sensor 8. The temperature sensing process is known per se. In brief, engine control device 9 obtains the impedance signal Vrpvs outputted from sensor drive circuit 52 at a predetermined sensing timing. Then, from impedance signal Vrpvs, the engine control device 9 calculate the impedance Rpvs of oxygen concentration sensing cell 24 by using a predetermined mathematical expression or data (such as a two dimensional map) representing a relationship between the impedance signal Vrpvs and the impedance Rpvs. Then, engine control device 9 calculates the temperature of oxygen concentration sensing cell 24 (or the temperature of gas sensor 8) in accordance with the impedance Rpvs. The thus-calculated temperature is used for the heater control process.

At the time of sensing impedance Rpvs, the system supplies the constant current −Iconst to oxygen concentration sensing cell 24 by turning on second switches SW2. After sensing the impedance, the system supplies the opposite polarity current +Iconst opposite in polarity to the impedance sensing current (−Iconst), to oxygen concentration sensing cell 24 by turning on third switches SW3. By so doing, the system can reduce a recovery time until a restoration of a normal state from a state in which the solid electrolyte member of oxygen concentration sensing cell 24 is oriented by the impedance sensing current, and the internal electromotive force is affected (the state in which the outputted electromotive force does not reflect the oxygen concentration difference correctly). The process for sensing impedance Rpvs of oxygen concentration sensing cell 24 is performed at regular time intervals of 100 msec, for example under the control of control section 55.

FIG. 4 shows the heater control process performed as the main routine. After a start of the heater control process, engine control device 9 first performs an initializing operation at a step S10. In this operation, engine control device 9 resets an overheat prevention flag and a sensor activation experience flag and an overheat prevention counter, to zero. The overheat prevention flag is a condition code for transferring control immediately to the overheat preventing process when the overheat prevention flag is on (=1). The sensor activation experience flag is a condition code representing the state in which gas sensor 8 is activated, and gas sensor 8 is in a normal gas measuring state (allowing the flow of the pump current Ip). The sensor activation experience flag is on (=1) when gas sensor 8 is activated. The overheat prevention counter is used for counting or measuring the heater overheat preventing time (Top, Tc1) shown in FIG. 3.

From S10, the engine control device 9 proceeds to a step S12, and reads the impedance Rpvs outputted from sensor drive circuit 52. Then, at a step S14, engine control device 9 examines whether the overheat prevention flag is ON (equal to one) or not. When the overheat prevention flag is ON, the engine control device 9 proceeds from S14 to a step S25 directly and starts the subroutine (the overheat preventing process of FIG. 5). When the overheat prevention flag is OFF, and hence the answer of S14 is NO, then engine control device 9 proceeds to a step S16.

At S16, engine control device 9 examines whether the sensor activation experience flag is ON (one) or not. From S16, the engine control device 9 proceeds to a step S18 when the sensor activation experience flag is ON and the answer of S16 is YES, and to a step 20 when it is not and the answer of S16 is NO.

At step S18, engine control device 9 calculates the heater application voltage (Vhrms) by the PI calculation. The PI calculation is known per se, as mentioned before, and the heater application voltage is calculated so as to hold the temperature of gas sensor 8 constant. In accordance with the thus-calculated heater application voltage, the engine control device 9 controls the supply of electricity to heater 43 through heater control circuit 60 (in the manner of the PWM control).

At step S20, engine control device 9 examines whether the impedance Rpvs obtained at S12 is smaller than a sensor activation judgment or judging threshold (which is set to 400Ω in this example). When the impedance Rpvs is smaller than the activation judging threshold (400Ω), the engine control device 9 considers that gas sensor 8 is in the normal active state, and sets the sensor activation experience flag to ON (one) at a step S22. From S22, engine control device 9 proceeds to step S18.

When the impedance Rpvs is greater than or equal to the activation judging threshold, the engine control device 9 proceeds from S20 to a step S24, and sets the application voltage (Vhrms) to heater 43 to the maximum effective voltage at S24. At the stage of S24, it is uncertain whether the impedance Rpvs is not normal because of trouble such as line disconnection, or merely the temperature of gas sensor 8 is low.

From S18 or S24, the engine control device 9 proceeds to step S25 and starts the heater overheat preventing process of FIG. 5 as the subroutine. When the subroutine of the heater overheat preventing process is finished, the engine control device 9 proceeds to a step S26, and examines, at S26, whether a predetermined impedance Rpvs reading cycle (10 msec in this example) of S12 has elapsed. Then, engine control device 9 returns to S12 when the answer of S12 becomes YES after the elapse of the Rpvs reading cycle, and waits when the answer of S12 is NO.

FIG. 5 shows the overheat preventing process performed as the subroutine. After a start of the overheat preventing process, engine control device 9 first examines whether the impedance Rpvs of oxygen concentration sensing cell 24 is smaller than the predetermined abnormality judgment or judging threshold (which is set equal to 400Ω in this example). When the impedance Rpvs is smaller than the abnormality judgment threshold (400Ω), then engine control device 9 proceeds from S50 to a step S52. At S52, engine control device 9 resets the overheat prevention counter to zero, and resets the overheat prevention flag to OFF (zero). After S52, engine control device 9 terminates the process of FIG. 5.

When impedance Rpvs is greater than or equal to the abnormality judgment threshold (400Ω) and hence the answer of S50 is NO, then engine control device 9 examines, at a step S54, whether the heater application voltage (Vhrms) is equal to the maximum effective voltage or not. If the answer of S54 is NO, the engine control device 9 terminates the process of FIG. 5.

In the case of YES of S54, the engine control device 9 judges that the heater application voltage is increased to the maximum effective voltage while the abnormal condition of S50 is met, and proceeds to a step S56. At S56, engine control device 9 increments the overheat prevention counter to start measuring time to stop the continuation of the application of the maximum effective voltage at the expiration of the overheat preventing time as shown in FIG. 3.

Then, engine control device 9 examines whether the sensor activation experience flag is ON (one) or not at a step S58. The judgment of S58 is performed to estimate the temperature condition of gas sensor 8 by checking the activation experience flag, and thereby to select a suitable amount of the heater overheat preventing time (Top, Tc1) in accordance with the temperature of gas sensor 8.

When the sensor activation experience flag is OFF and hence the answer of S58 is NO, then engine control device 9 proceeds to a step S60. At S60, engine control system 9 assumes that gas sensor 8 is not yet activated and still cold, and examines whether the overheat prevention counter is greater than or equal to an amount of time or interval Top.

When the overheat prevention counter is greater than or equal to Top and hence the answer of S60 is YES, the engine control device 9 judges that the application of the maximum effective voltage is continued for a time duration longer than or equal to Top, and proceeds to a step S62. At S62, engine control device 9 delivers a command signal (in the form of the heater on signal) to decrease the heater application voltage (Vhrms) to the low effective voltage (lower effective voltage), to heater control circuit 60, and sets the heater overheat prevention flag to one. In this example, this command signal commands a decrease of the heater application voltage from the maximum effective voltage to the lower effective voltage (8V) by decreasing the duty cycle from a greater value corresponding to the maximum effective voltage to a lower value corresponding to the lower effective voltage. In response to this command signal in the form of the heater on signal, the heater control circuit 60 applies the lower effective voltage to heater 43. After S62, engine control device 9 terminates the overheat preventing process of FIG. 5 and returns to the main routine of FIG. 4.

The overheat prevention flag is set to one at S62. Therefore, when engine control device 9 returns to the main routine of FIG. 4, the engine control device 9 can proceed from S14 directly to S25, and continue the heater overheat preventing process of FIG. 5. When step S62 is reached, there is a possibility that the abnormality such as the disconnection of Vs+ line continues to be present. Therefore, the overheat prevention flag is set to one at S62.

When the sensor activation experience flag is ON and hence the answer of S58 is YES, then engine control device 9 proceeds to a step S64. At S64, engine control system 9 assumes that gas sensor 8 is already activated and controlled in the PI control mode, and the temperature of gas sensor 8 is increased to the operating temperature (830° C., for example), and examines whether the overheat prevention counter is greater than or equal to an amount of time or interval Tc1.

When the overheat prevention counter is greater than or equal to Tc1 and hence the answer of S64 is YES, the engine control device 9 judges that the application of the maximum effective voltage is continued for a time duration longer than or equal to Tc1, and proceeds to a step S66. At S66, engine control device 9 delivers the command signal (in the form of the heater on signal) to decrease the heater application voltage (Vhrms) to the low effective voltage (lower effective voltage), to heater control circuit 60, and sets the heater overheat prevention flag to one. In this example, this command signal commands the decrease of the heater application voltage from the maximum effective voltage to the lower effective voltage (8V) by decreasing the duty cycle from the greater value corresponding to the maximum effective voltage to the lower value corresponding to the lower effective voltage. In response to this command signal in the form of the heater on signal, the heater control circuit 60 applies the lower effective voltage to heater 43. After S66, engine control device 9 terminates the overheat preventing process of FIG. 5 and returns to the main routine of FIG. 4. At S66, the overheat prevention flag is set to one for the same reason as in step S62.

In this embodiment, step S12 corresponds to "impedance sensing step", and step S50 corresponds to "impedance condition examining step" (or "impedance abnormality judging step"). Step S54 corresponds to "voltage condition examining step" (or "voltage application judging step"). Steps S56, S58, S60 and S64 correspond to "duration measuring step" (or "voltage application condition judging step"). The operations of engine control device 9 and/or heater control circuit 60 according to steps S62 and S64 correspond to "voltage decreasing step" (or "lower effective voltage applying step"). Step S20 corresponds to "activation judging step". The operation of setting the amount of the heater overheat preventing time in dependence on the judgment of S58 corresponds to "time setting step".

The present invention is not limited to the above-mentioned embodiment. Various variations and modifications are possible within the purview of the present invention. For example, the sensing element 10 may be any of various types besides the full range air fuel ratio employed in the illustrated example. The present invention is applicable to a gas sensor, such as a NOx sensor, in which another cell is added to sensing element, and there are formed two of measurement chambers. In the illustrated embodiment, the gas sensor control apparatus is incorporated in ECU 5. However, it is optional to provide the gas sensor control apparatus separate from ECU 5. For example, the gas sensor control apparatus is provided between the gas sensor 8 and ECU 5, and constructed to include the sensor control circuit 2, the heater control circuit 60 and a microcomputer capable of executing the heater control process and the heater overheat preventing process. The microcomputer may be formed on or in a circuit board including the microcomputer alone or together with the circuits 2 and 60. In the illustrated example, the activation judging threshold used in step S20 and the abnormality judging threshold used in step S50 are equal to each other. However, it is possible to set the activation judging threshold and the abnormality judging threshold at two different amounts, respectively.

According to the illustrated embodiment, a gas sensor control apparatus is adapted to be connected with a gas sensor for sensing the concentration of a specified gas, or the gas sensor control apparatus includes a connecting section (which may include one or more terminals) adapted to be connect with the gas sensor. Alternatively, the gas sensor control apparatus may be a gas sensor control system including the gas sensor. The gas sensor may be a sensor including at least one cell (monitored cell) including a solid electrolyte member and a pair of electrodes separated from each other by the solid electrolyte member. The gas sensor control apparatus comprises: a heater regulating section to control the supply of electricity to a heater included in the gas sensor; an impedance sensing section to sense an impedance of the (monitored) cell of the gas sensor, from an output of the cell; a sensor (impedance) condition examining section to examine whether the impedance sensed by the impedance sensing section is greater than or equal to a predetermined abnormality judging threshold; a heater (voltage) condition examining section to examine whether a maximum effective voltage (or a higher effective voltage higher than or equal to a predetermined level which may be equal to the maximum effective voltage as in the illustrated, example) is applied to the heater, when the impedance is judged to be greater than or equal to the predetermined abnormality judging threshold; a time duration measuring section to examine whether an application time duration of application of the maximum effective voltage (or the higher effective voltage) to the heater becomes equal to or longer than a predetermined heater overheat preventing time; and a voltage decreasing section to command the heater regulating section to decrease the voltage applied to the heater to a lower effective voltage and continue the application of the voltage to the heater at the lower effective voltage which is lower than the maximum effective voltage and which is so set as to hold the temperature of the cell higher than or equal to a predetermined temperature value such as 500° C. when the application time duration becomes equal to or longer than the predetermined heater overheat preventing time. It is possible to determine whether the lower effective voltage to hold the temperature of the monitored cell higher than or equal to 500° C. is applied to the heater or not, by examining the impedance sensed through the monitored cell to determine whether the sensed impedance is at a value which can be assumed when the temperature is equal to or higher than 500° C.

According to one of various possible interpretations of the embodiment, a gas sensor control apparatus has a basic construction which comprises: a heater regulating section to supply an electric power or electricity to a heater included in a gas sensor for sensing a concentration of a specified gas; an impedance sensing section to sense an impedance of a (monitored) cell of the gas sensor; and a controlling section which is configured to check a first condition (S50: NO) which is satisfied when the impedance is greater than or equal to a predetermined abnormality judging threshold, to check a second condition (S54: YES) which is satisfied when the electric power supplied to the heater is higher than or equal to a predetermined higher power level (such as the maximum effective voltage), to measure a continuance (or time duration) of a third condition which is satisfied when the first and second conditions are both satisfied simultaneously (S56), and to decrease the electric power (or the quantity of electricity) supplied to the heater by the heater regulating section, to a lower power level lower than the higher power level when the continuance of the third condition reaches a predetermined overheat preventing time. The thus-constructed gas sensor control apparatus may further comprise any one or more of the following features.

(1) The controlling section of the basic construction may be configured to adjust the predetermined overheat preventing time in accordance with a starting (temperature) state of the gas sensor before or just before a start of the continuance of the third condition. (2) The lower power level may be so set as to hold the temperature of the gas sensor at such a higher temperature level preventing adherence of a substance, such as carbon, contained in a measurement gas to the gas sensor. (3) The controlling section may be configured to control the electric power supplied to the heater with the heater regulating section normally in a normal heater control mode (such as PI control mode at S16) in accordance with the impedance of the (monitored) cell of the gas sensor (for example, so as to decrease a deviation between the sensed actual impedance and a desired target impedance). (4) The controlling section may be configured to terminate the normal heater control mode and instead to start a limiting heater control mode (including a limiting time mode until the end of the overheat preventing time and a limiting power mode with the lower power level after the end of the overheat preventing time) when the first and second conditions become satisfied. (5) The controlling section may be configured to terminate the limiting heater control mode and instead resumes the normal heater control mode when the first condition becomes unsatisfied.

This application is based on a prior Japanese Patent Application No. 2008-285054 filed on Nov. 6, 2008. The entire contents of this Japanese Patent Application are hereby incorporated by reference.

Although the invention has been described above by reference to certain embodiments of the invention, the invention is not limited to the embodiments described above. Modifications and variations of the embodiments described above will occur to those skilled in the art in light of the above teachings. The scope of the invention is defined with reference to the following claims.

What is claimed is:
1. A gas sensor control apparatus for controlling a gas sensor for sensing a concentration of a specified gas, the gas sensor including a cell including a solid electrolyte member and a pair of electrodes formed on the solid electrolyte member, the gas sensor control apparatus comprising:
 an electronic controller comprising:
  a heater regulating section to control a supply of electricity to a heater included in the gas sensor;
  a sensor control circuit to sense an impedance of the cell of the gas sensor, from an output of the cell;

an impedance condition examining section to examine whether the impedance sensed by the sensor control circuit is greater than or equal to a predetermined abnormality judging threshold;

a voltage condition examining section to examine whether a maximum effective voltage is applied to the heater, when the impedance is judged to be greater than or equal to the predetermined abnormality judging threshold;

a duration measuring section to examine whether an application time duration of application of the maximum effective voltage to the heater becomes equal to or longer than a predetermined heater overheat preventing time; and a voltage decreasing section to command the heater regulating section to apply, to the heater, a lower effective voltage which is lower than the maximum effective voltage and which is so set as to hold the temperature of the cell higher than or equal to 500° C. when the application time duration becomes equal to or longer than the predetermined heater overheat preventing time.

2. The gas sensor control apparatus as claimed in claim 1, wherein the electronic controller further comprises:

an activation judging section to examine whether the impedance sensed by the impedance sensing section is smaller than or equal to an activation judging threshold, and judges that the gas sensor is activated when the impedance is smaller than or equal to the activation judging threshold; and a time setting section to set the heater overheat preventing time equal to a first amount when the impedance is smaller than or equal to the activation judging threshold, and to set the heater overheat preventing time equal to a second amount longer than the first amount when the impedance is greater than the activation judging threshold.

3. The gas sensor control apparatus as claimed in claim 1, wherein the lower effective voltage is so set as to hold the temperature of the cell higher than or equal to 700° C.

* * * * *